United States Patent
Ito et al.

(10) Patent No.: US 7,802,507 B2
(45) Date of Patent: Sep. 28, 2010

(54) AUTOMATIC SLICED PIECE FABRICATING APPARATUS AND AUTOMATIC SLICED PIECE SAMPLE FABRICATING APPARATUS

(75) Inventors: Tetsumasa Ito, Chiba (JP); Tatsuya Miyatani, Chiba (JP); Koji Fujimoto, Chiba (JP)

(73) Assignee: Seiko Instruments Inc., Chiba (JP)

( * ) Notice: Subject to any disclaimer, the term of this patent is extended or adjusted under 35 U.S.C. 154(b) by 661 days.

(21) Appl. No.: 11/651,714

(22) Filed: Jan. 10, 2007

(65) Prior Publication Data

US 2007/0204734 A1 Sep. 6, 2007

(30) Foreign Application Priority Data

Jan. 18, 2006 (JP) .............................. 2006-009466

(51) Int. Cl.
*G01N 1/04* (2006.01)
*G01N 1/06* (2006.01)

(52) U.S. Cl. ........................... 83/170; 83/169; 83/915.5

(58) Field of Classification Search ............... 83/14–15, 83/169–171, 22, 915.5; 62/51.1, 320; 73/863.11
See application file for complete search history.

(56) References Cited

U.S. PATENT DOCUMENTS

| | | | | |
|---|---|---|---|---|
| 3,191,476 | A * | 6/1965 | McCormick | ................. 83/169 |
| 3,203,290 | A | 8/1965 | Ashby | |
| 3,236,133 | A * | 2/1966 | De Pas | ........................ 83/170 |
| 3,978,686 | A | 9/1976 | Lechner et al. | |
| 4,284,894 | A * | 8/1981 | Sitte et al. | ................. 250/443.1 |
| 5,960,640 | A | 10/1999 | Teppke | |
| 6,387,653 | B1 * | 5/2002 | Voneiff et al. | ............ 435/40.52 |
| 2004/0206093 | A1 | 10/2004 | Dorenkamp et al. | |
| 2006/0133950 | A1 * | 6/2006 | Teppke | ........................ 422/28 |
| 2007/0157786 | A1 * | 7/2007 | Miyatani et al. | .............. 83/651 |
| 2008/0181814 | A1 * | 7/2008 | Teppke | ........................ 422/28 |

FOREIGN PATENT DOCUMENTS

| | | |
|---|---|---|
| EP | 1 498 718 A1 | 3/2003 |
| JP | 2004-317515 | 11/2004 |
| WO | WO 00/62035 | 10/2000 |
| WO | WO 03/083445 | * 10/2003 |

OTHER PUBLICATIONS

European Search Report EP App. No. 07250155.4-1234, Apr. 12, 2007.

* cited by examiner

*Primary Examiner*—Laura M. Lee
(74) *Attorney, Agent, or Firm*—Brinks Hofer Gilson & Lione

(57) ABSTRACT

To fabricate automatically a high quality sliced piece by preventing a temperature change of a surface of an enveloped block, there is provided an automatic sliced piece fabricating apparatus including a fixed base for mounting to fix an enveloped block, cutting means including a cut blade arranged on the fixed base for cutting out a sliced piece from the enveloped block by moving the cut blade and the fixed base relative to each other, a cabinet for containing the fixed base and the cutting means at inside thereof, sliced piece carrying means for carrying the cut-out sliced piece to outside of the cabinet, and temperature adjusting means for adjusting at least a surrounding temperature of the enveloped block to a predetermined temperature by supplying cold wind a temperature of which is controlled from outside at inside of the cabinet.

11 Claims, 4 Drawing Sheets under the enveloped block is cooled, the temperature of the vicinity of the surface cannot easily be lowered to a temperature which can firmly be cut.

AUTOMATIC SLICED PIECE FABRICATING APPARATUS AND AUTOMATIC SLICED PIECE SAMPLE FABRICATING APPARATUS

This application claims priority under 35 U.S.C. §119 to Japanese Patent Application No. JP2006-009466 filed Jan. 18, 2006, the entire content of which is hereby incorporated by reference.

BACKGROUND OF THE INVENTION

1. Field of the Invention

The present invention relates to an automatic sliced piece fabricating apparatus for automatically fabricating a sliced piece used in a scientific experiment or microscopic observation and an automatic sliced piece sample fabricating apparatus for automatically fabricating a sliced piece sample by fixing a fabricated sliced piece on a base plate.

2. Description of the Related Art

In a related art, there is carried out a toxic test or a pathological inspection on an experimental animal prior to a clinical test in developing a new drug. The test or the inspection is carried out by using a sliced piece sample fixed with a sliced piece having a thickness of several μm, (for example, 3 μm through 5 μm) on a base plate of a slide glass or the like. There is used a sliced piece sliced for a pathological inspection by subjecting an experimental animal of a mouse or a rabbit administered with a drug to autopsy. Further, sliced pieces are fabricated for respective various portions (for example, brain or lung or the like).

A microtome is known as an apparatus for fabricating such a sliced piece sample. Here, an explanation will be given of a general method of fabricating a sliced piece sample by utilizing a microtome.

First, an enveloped block in a block state is fabricated by subjecting a living body sample of a living thing, such as an animal or the like, fixed by formalin to paraffin substitution, and thereafter, further hardening a surrounding thereof by paraffin to be solid. Next, rough machining is carried out by setting the enveloped block to a microtome constituting an exclusive slicing apparatus. By the rough machining, a surface of the enveloped block becomes a smooth face and there is brought about a state of exposing the enveloped living body sample constituting an object of experiment or observation at the surface.

After finishing the rough machining, regular machining is carried out. This is a step of slicing the enveloped block to be extremely thin by the above-described thickness by a cutting blade provided to the microtome. Thereby, the sliced piece can be provided. At this occasion, by slicing the enveloped block as thin as possible, the thickness of the sliced piece can be made to be proximate to a thickness of cell level and therefore, further accurate observation data can be provided. Therefore, it is requested to fabricate the sliced piece having a thickness as thin as possible. Further, the regular cutting is continuously carried out until providing a necessary number of sheets of the sliced pieces.

Next, there is carried out an elongating step for elongating the sliced piece provided by the regular machining. That is, the sliced piece fabricated by the regular machining is brought into a wrinkled state or a rounded state (for example, U-like shape) since the sliced piece is sliced to the extremely thin thickness as described above. Hence, it is necessary to elongate the sliced piece by removing wrinkle or roundness by the elongating step.

Generally, the sliced piece is elongated by utilizing water and hot water. First, the sliced piece provided by the regular machining is floated on water. Thereby, large wrinkle or roundness of the sliced piece can be removed while preventing portions of paraffin enveloping the living body sample from being stuck. Thereafter, the sliced piece is floated on hot water. Thereby, the sliced piece is easy to be elongated and therefore, remaining wrinkle or roundness which cannot be removed by being elongated by water can be removed.

Further, the sliced piece finished with the elongation by hot water is scooped by a base plate of slide glass or the like to be mounted on the base plate. Further, when the elongation is insufficient assumedly at the time point, the sliced piece is mounted on a hot plate or the like along with the base plate and is heated further. Thereby, the sliced piece can further be elongated.

Finally, the base plate mounted with the sliced piece is put into a dehydrator to be dried. By the drying, moisture adhered by the elongation is evaporated and the sliced piece is fixed onto the base plate. As a result, the sliced piece sample can be fabricated.

Here, although paraffin used as the enveloped block having a melting point of a temperature as low as possible is preferable to prevent a living body tissue from being denatured, on the other hand, it is preferable that the melting point is as high as possible in order to prevent softening under a temperature of a slicing operational environment. Hence, paraffin having a melting point of about 60° C. is used in reality by compromising both requirements.

However, even when such paraffin is used, the temperature of the operational environment constitutes a limit by 20° C. corresponding to a temperature of starting to soften paraffin at the lowest temperature and therefore, there is a concern of gradually softening paraffin with an elapse of time. When paraffin is assumedly softened, slicing becomes difficult, a sliced piece cut out from an enveloped block is broken or easy to be deformed. Hence, in order to prevent such a drawback as less as possible, generally, an enveloped block is previously cooled by a refrigerator or iced water or the like. Further, a sliced piece is cut out by setting the cooled enveloped block to a microtome immediately before being cut.

However, even when the above-described method is adopted, although a problem is not posed at start, the temperature of the enveloped block rises with time and therefore, the enveloped block is elongated, and hardness or friction coefficient of paraffin is gradually changed. That is, cutting cannot be carried out always under the same condition. Therefore, in fabricating the sliced piece, fine adjustment of a cutting amount of the microtome, or adjustment of temporarily cooling a surface of the enveloped block by ice is obliged to be carried out auxiliarily by empirically determining a thickness or a shape from the sliced piece cut out by an operator.

Hence, in order to resolve such a drawback as less as possible, there is proposed an apparatus of integrating a Pertier element at a portion of holding an enveloped block and cooling a bottom face of the enveloped block by the Pertier element (for example, JP-A-2004-317515). According to the apparatus, the sliced piece can be cut out in a state of restraining a temperature rise of the previously cooled enveloped block as low as possible.

However, according to the related art apparatus, the following problem still remains.

That is, according to the apparatus, the bottom face of the enveloped block is cooled by the Pertier element and therefore, it is difficult to control a temperature at a vicinity of a surface of the enveloped block (for example, a range of several μm from the surface). That is, since the thermal conduction coefficient of paraffin is small, even when the bottom face is cooled, it is difficult to control a surface temperature related to cutting. Thereby, in fabricating the sliced piece, heat generated by a friction with a cutting blade cannot be absorbed and a good quality sliced piece cannot uniformly be fabricated by the influence of the heat. That is, the hardness or the friction coefficient of paraffin is changed by the heat and the sliced piece is liable to be deformed or broken. Therefore, the auxiliary adjustment based on hunch or experience is obliged to be carried out manually. Particularly, the fact constitutes a factor of remarkably hampering automation of the sliced piece.

SUMMARY OF THE INVENTION

The invention has been carried in view of such a situation and it is an object thereof to provide an automatic sliced piece fabricating apparatus capable of automatically fabricating a high quality sliced piece by preventing a temperature change of a surface of an enveloped block and an automatic sliced piece sample fabricating apparatus having the same.

The invention provides the following means in order to resolve the above-described problem.

According to the invention, there is provided an automatic sliced piece fabricating apparatus for cutting out a sliced piece in a sheet-like shape by cutting an enveloped block enveloped with a living body sample by an enveloping agent by a predetermined thickness, the automatic sliced piece fabricating apparatus comprising a fixed base for mounting to fix the enveloped block, cutting means including a cutting blade arranged on the fixed base for cutting out the sliced piece from the enveloped block by moving the cutting blade and the fixed base relative to each other, a cabinet for containing the fixed base and the cutting means at inside thereof, sliced piece carrying means for carrying the cut-out sliced piece outside of the cabinet, and temperature adjusting means for adjusting at least a surrounding temperature of the enveloped block to a predetermined temperature by supplying cold wind a temperature of which is controlled from outside to inside of the cabinet.

According to the automatic sliced piece fabricating apparatus according to the invention, first, for example, the previously cooled enveloped block is mounted on the fixed base manually or by a robot or the like. When the enveloped block is mounted thereon, the cutting means cuts (slices) the enveloped block in the sheet-like shape by a predetermined thickness (for example, as extremely thin as 5 μm) by moving the fixed base and the cutting blade relative to each other. Thereby, the sliced piece can be cut out to be fabricated. Further, the fabricated sliced piece is carried outside of the cabinet by the sliced piece carrying means.

In this way, since the cutting means and the sliced piece carrying means are provided, a plurality of sheets of the sliced pieces can automatically be fabricated from the enveloped block mounted on the fixed base to be successively carried outside of the cabinet. Further, by successively mounting a plurality of the enveloped blocks on the fixed base, respective pluralities of sheets of the sliced pieces can automatically be fabricated from the plurality of enveloped blocks to be carried outside of the cabinet.

Particularly, in cutting the enveloped block, the temperature adjusting means supplies the cold wind, the temperature of which is controlled inside of the cabinet and carries out the temperature adjustment such that at least the temperature of the surrounding of the enveloped block becomes the predetermined temperature. Therefore, even when the enveloped block is previously cooled, different from the related art, the surface temperature is difficult to rise with an elapse of time.

Particularly, although in the related art, only the lower face of the enveloped block is simply cooled, the temperature adjusting means adjusts the surrounding temperature of the enveloped block directly by supplying the cold wind. Therefore, even when paraffin or the like having the small heat conduction coefficient is used as the enveloping agent, the temperature of the surface is easy to be adjusted. In addition thereto, also by utilizing air having a small heat amount per volume as the cold wind, the temperature is easy to be adjusted. Further, only the cold wind is utilized and therefore, an influence is not effected at all to cutting out the sliced piece by the cutting means.

In this way, since the temperature adjusting means is provided, during a time period until finishing to fabricate the sliced piece after mounting the sliced piece on the fixed base, the temperature change of the surface of the enveloped block can be restrained as small as possible. Therefore, a mechanical property of hardness, friction coefficient or viscosity of the enveloping agent of paraffin or the like is difficult to be changed. As a result, the enveloped block can be cut under the same condition and a uniform and high quality sliced piece can be fabricated.

As described above, according to the automatic sliced piece fabricating apparatus of the invention, the temperature change of the surface of the enveloped block can be restrained as small as possible by supplying the cold wind and therefore, the high quality and uniform sliced piece can automatically be fabricated. Further, since the cold wind is utilized, different from the case of utilizing the Pertier element of the related art, dew condensation is difficult to be brought about.

Further, according to the invention, there is provided the automatic sliced piece fabricating apparatus, wherein the temperature controlling means carries out a temperature adjustment such that a surrounding temperature of the enveloped block is converged in a range of 5° C. through 20° C. in the above-described automatic sliced piece fabricating apparatus of the invention.

According to the automatic sliced piece fabricating apparatus according to the invention, the temperature is adjusted such that the surrounding temperature of the enveloped block is converged in the range of 5° C. through 20° C. and therefore, the temperature is adjusted such that also the surface temperature of the enveloping agent of paraffin or the like is converged similarly in the temperature range of 5° C. through 20° C. Particularly, paraffin is generally used as the enveloping agent, and when the temperature of the paraffin becomes equal to or higher than 5° C. through 20° C., the paraffin starts to be softened and the mechanical property is liable to be changed abruptly. However, the surface temperature of the enveloping agent is adjusted to be converged within the temperature range by temperature adjusting means as described above and therefore, even when paraffin is used as the enveloping agent, the mechanical property of paraffin can be maintained constant. Therefore, the enveloped block can further be cut under the same condition and the uniform sliced piece is easy to be provided.

Further, according to the invention, there is provided the automatic sliced piece fabricating apparatus, wherein the temperature adjusting means comprises a supply pipe line for supplying the cold wind to the cabinet, an exhaust pipe line for exhausting a gas from inside of the cabinet to the outside, and cold wind supplying means for recirculating the gas exhausted from the exhaust pipe line from the supply pipe line into the cabinet as the cold wind.

According to the automatic slice piece fabricating apparatus according to the invention, the cold wind supplying means supplies the cold wind into the cabinet through the supply pipe line. The supplied cold wind cools the surrounding of the enveloped block inside of the cabinet. Thereby, at least the surface of the enveloped block is cooled. Further, the gas inside of the cabinet is exhausted to the outside of the cabinet by passing through the exhaust pipe line and is continuously recirculated into the cabinet as the cold wind without interruption by the cold wind supplying means. That is, the cold wind flows while being circulated in order of the supply pipe line, the cabinet and the exhaust pipe line by the cold wind supplying means.

Therefore, the surrounding of the enveloped block carried into the cabinet can efficiently be cooled and the surface of the enveloped block can further be cooled. Further, since the cold wind is circulated, the cold wind can be supplied efficiently and low cost formation can be achieved.

Further, according to the invention, there is provided the automatic sliced piece fabricating apparatus further comprising cold wind blowing means arranged inside of the cabinet for locally blowing second cold wind, the temperature of which is controlled to a surface of the enveloped block in any of the above-described sliced piece fabricating apparatus of the invention.

According to the automatic sliced piece fabricating apparatus according to the invention, in cutting the enveloped block, the cold wind blowing means locally blows the second cold wind, the temperature of which is controlled to the surface of the enveloped block inside of the cabinet. Thereby, the surface of the enveloped block can further firmly be cooled. Therefore, rise of the surface temperature of the enveloped block can further be restrained and the further uniform and high quality sliced piece can firmly be fabricated.

Further, according to the invention, there is provided the automatic sliced piece fabricating apparatus, wherein the cold wind blowing means comprises temperature measuring means for measuring the surface temperature of the enveloped block in noncontact, and second temperature adjusting means for adjusting the temperature of the second cold wind such that the surface temperature of the enveloped block becomes a desired temperature based on the temperature measured by the temperature measuring means in the above-described automatic sliced piece fabricating apparatus of the invention.

According to the sliced piece fabricating apparatus according to the invention, the temperature measuring means of a radiation pyrometer or the like measures the surface temperature of the enveloped block to which the second cold wind is blown. Further, the second temperature adjusting means controls the temperature of the second cold wind by a feedback control such that the surface of the enveloped block becomes a desired temperature based on the measured temperature. Thereby, the surface temperature of the enveloped block can be controlled further highly accurately. Further, since the temperature measuring means measures the surface temperature of the enveloped block in a noncontact state, an influence is not effected at all on cutting out the sliced piece by the cutting means.

Further, according to the invention, there is provided the automatic sliced piece fabricating apparatus, wherein the fixed base is integrated with a fixed base cooling mechanism for cooling the enveloped block by being brought into contact with the enveloped block in the above-described sliced piece fabricating apparatus of the invention.

According to the automatic sliced piece fabricating apparatus according to the invention, the fixed base is integrated with the fixed base cooling mechanism and therefore, the enveloped block mounted on the fixed base can further be cooled from the side of the fixed base. Therefore, a cooling effect of the second cold wind blown by the cold wind blowing means can be promoted, and the cooling efficiency can be promoted.

Further, according to the invention, there is provided the automatic sliced piece fabricating apparatus, wherein the cutting means comprises a cutting blade cooling mechanism for cooling the cutting blade by being brought into contact with the cutting blade in any of the above-described automatic sliced piece fabricating apparatus of the invention.

According to the automatic sliced piece fabricating apparatus according to the invention, the cutting blade per se can be cooled by the cutting blade cooling mechanism and therefore, in cutting out the sliced piece from the enveloped block, the sliced piece can be prevented from being softened by the temperature of the cutting blade. Therefore, the sliced piece can be prevented from sticking to the cutting blade and deformation or the like of the sliced piece owing to the sticking can be prevented. Further, since the sliced piece is difficult to stick to the cutting blade, the sliced piece is easy to be carried outside of the cabinet by the sliced piece carrying means.

Further, according to the invention, there is provided an automatic sliced piece sample fabricating apparatus comprising any of the above-described automatic sliced piece fabricating apparatus of the invention, block carrying means for carrying the enveloped block from outside of the cabinet onto the fixed base, elongating means for elongating the sliced piece carried by the sliced piece carrying means at least by dipping the sliced piece into a liquid, and transcribing means for transcribing the elongated sliced piece onto a base plate to fabricate a sliced piece sample.

According to the automatic sliced piece sample fabricating apparatus according to the invention, since the block carrying means is provided, a plurality of the enveloped blocks can successively carried onto the fixed base simply and easily. Further, the sliced piece carried outside of the cabinet by the sliced piece carrying means is dipped to be elongated at inside of the liquid of water or the like provided to the elongating means. That is, the sliced piece dipped in water is elongated since the sliced piece is brought into a state of being elongated by removing wrinkle or roundness brought about in cutting by the surface tension. The sliced piece elongated by the elongating means is transcribed onto the base plate of slide glass or the like by the transcribing means. Thereby, the sliced piece sample transcribed with the sliced piece on the base plate can be fabricated.

Particularly, the sliced piece fabricated by the automatic sliced piece fabricating apparatus is the uniform and high quality sliced piece and therefore, also the high quality sliced piece sample can similarly be fabricated. Therefore, accuracy of various tests or inspections using the sliced piece sample can further be promoted and reliability can be promoted.

According to the automatic sliced piece fabricating apparatus according to the invention, the temperature change of the surface of the enveloped block can be restrained as small as possible and therefore, the high quality and uniform sliced piece can automatically be fabricated.

Further, according to the automatic sliced piece sample fabricating apparatus according to the invention, the uniform and high quality sliced piece is used by being fabricated under the same temperature condition and therefore, the high quality sliced piece sample can similarly be fabricated automatically. Therefore, accuracy of various tests or inspections using the sliced piece sample can further be promoted and reliability can be promoted.

DETAILED DESCRIPTION OF THE PREFERRED EMBODIMENTS

An explanation will be given of a first embodiment of an automatic sliced piece fabricating apparatus and an automatic sliced piece sample fabricating apparatus according to the invention in reference to FIG. 1 through FIG. 4 as follows. Further, according to the embodiment, an explanation will be given by taking an example of a living body tissue sampled from an experimental animal of a mouse or the like as a living body sample.

An automatic sliced piece sample fabricating apparatus 1 according to the embodiment is an apparatus of fabricating a sliced piece sample H by transcribing a sliced piece B1 fabricated with an enveloped block B enveloped with a living body tissue S by an enveloping agent onto a slide glass (base plate) G.

Figure 1:
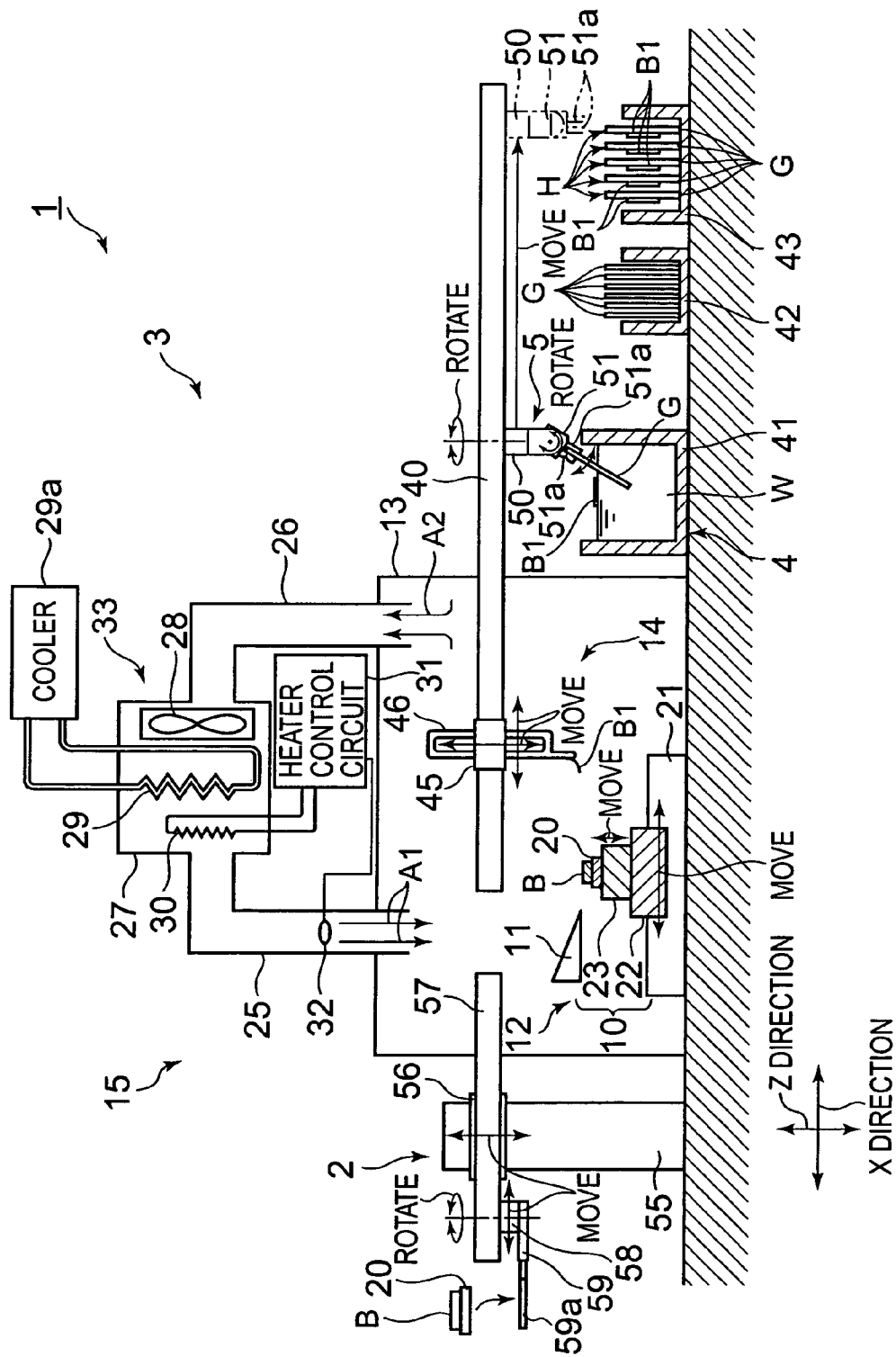
FIG. 1 is a constitution view showing a first embodiment of an automatic sliced piece sample fabricating apparatus and an automatic sliced piece fabricating apparatus according to the invention.

That is, as shown by FIG. 1, the automatic sliced piece sample fabricating apparatus 1 includes a block handling robot (block carrying means) 2 for carrying the enveloped block B from outside of a casing 13 of an automatic sliced piece fabricating apparatus 3 onto a fixed base 10, the automatic sliced piece fabricating apparatus 3 for fabricating the sliced piece B1 from the carried enveloped block B, an elongating mechanism (elongating means) 4 for elongating the sliced piece B1 carried by a sliced piece handling mechanism (sliced piece carrying means) 14 of the automatic sliced piece fabricating apparatus 3 at least by dipping the sliced piece B1 in water (liquid) W, and a slide glass handling robot (transcribing means) 5 for fabricating the sliced piece sample H by transcribing the elongated sliced piece B1 onto the slide glass G.

The automatic sliced piece fabricating apparatus 3 is an apparatus of cutting the enveloped block B by a predetermined thickness to thereby cut out to fabricate the slice piece B1 in a sheet-like shape.

That is, the automatic sliced piece fabricating apparatus 3 includes the fixed base 10 for mounting to fix the enveloped block B carried by the block handling robot 2, a cut mechanism (cutting means) 12 including a cutting blade 11 arranged on the fixed base 10 for cutting out the sliced piece B1 from the enveloped block B by moving the cutting blade 11 and the fixed base 10 relative to each other. The casing (cabinet) 13 contains the fixed base 10 and the cut mechanism 12 at inside thereof, the sliced piece handling mechanism (sliced piece carrying means) 14 for carrying the cut-out sliced piece B1 outside of the casing 13, and temperature adjusting means 15 for adjusting at least a temperature of a surrounding of the enveloped block B to a predetermined temperature by supplying cold wind A1, a temperature of which is controlled from outside at inside of the casing 13.

Figure 2:
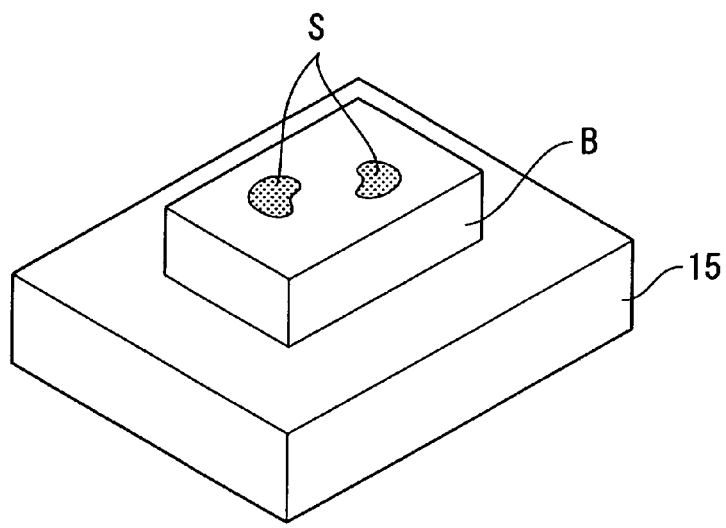
FIG. 2 is a perspective view of an enveloped block used in the automatic sliced piece sample fabricating apparatus shown in FIG. 1.

According to the enveloped block B, as shown by FIG. 2, paraffin is made to substitute for moisture at inside of the living body tissue S fixed by formalin. Thereafter a surrounding thereof is hardened in a block-like shape by an enveloping agent of paraffin or the like. Thereby, the living body tissue S is enveloped inside of paraffin. Further, the enveloped block B is mounted on a cassette 20 formed in a box-like shape.

As shown by FIG. 1, the fixed base 10 includes X stage 22 movable along a guide rail 21 extended in X direction directed to the fixed cutting blade 11, and Z stage 23 attached to X stage 22 and movable in Z direction directed in a vertical direction. Further, the guide rail 21 extends to an opposed side exceeding the cutting blade 11. X stage 22 is made to move reciprocally on the guide rail 21 by a motor or the like, not illustrated. Further, X stage 23 is integrated with a piezoelectric electric element or the like, not illustrated, inside thereof, and a height thereof is controlled to be elevated by every constant amount in Z direction by being applied with a voltage. At this occasion, Z stage 23 is elevated by the constant amount at each time of reciprocating the guide rail 21 by one reciprocation by X stage 22.

Thereby, the enveloped block B mounted on the fixed base 10, that is, on Z stage 23, is moved toward the cutting blade 11 in accordance with movement of X stage 22 to be cut by the cutting blade 11. At this occasion, since the height is controlled by Z stage 23, a surface thereof is cut by a predetermined thickness (that is, 5 μm). As a result, the sliced piece B1 in the sheet-like shape is fabricated. A detailed explanation will be given thereof later. Further, by the reciprocal movement of X stage 22 and elevation of Z stage 23 in synchronism with the reciprocal movement, a plurality of the sliced pieces B1 are successively fabricated from the enveloped block B.

The guide rail 21, X stage 22, Z stage 23 and the cutting blade 11 constitute the cut mechanism 12. Further, although according to the embodiment, there is constructed a constitution of cutting the enveloped block B by fixing the cutting blade 11 and moving the side of the fixed base 10 relative to the cutting blade 11, the cut mechanism 12 is not limited to the constitution. For example, the fixed base 10 may be fixed and the cutting blade 11 may be moved relative to the fixed base 10, and the cut mechanism 12 may be constituted by moving both of the fixed base 10 and the cutting blade 11. At any rate, the fixed base 10 and the cutting blade 11 may be constituted to move relative to each other.

The casing 13 is formed in a box-like shape containing at least the fixed base 10 and the cut mechanism 12. Side faces thereof are respectively formed with outlets/inlets, not illustrated, for putting in and out portions of the block handling robot 2 and sliced piece handling mechanism 14.

Further, an upper portion of the casing 13 is attached with one end side of a supply pipe line 25 for supplying the cold wind A1 from outside and one end side of an exhaust pipe line 26 for exhausting gas A2 from inside of the casing 13 to the outside. The other end side of the supply pipe line 25 and the other end side of the exhaust pipe line 26 are connected to side faces of a box 27 respectively in an opposed form. The inside of the box 27 includes a fan 28, a heat exchanger 29 connected to a cooler 29a and a heater 30 successively from a side of the exhaust pipe line 26.

The fan 28 sucks the gas A2 inside of the casing 13 through the exhaust pipe line 26 and blows the sucked gas A2 to the heat exchanger 29. The heat exchanger 29 absorbs heat of the blown gas A2 to change it into the cold wind A1. Further, a heater 30 is electrically connected to a heater control circuit 31 to control a heat generating amount. The heater control circuit 31 controls the heat generating amount of the heater 30 by receiving a result of measurement from a temperature sensor 32 attached to inside of the supply pipe line 25. That is, the cold wind A1 changed by the heat exchanger 29 is heated by the heater 30 to adjust a temperature thereof, thereafter, supplied to inside of the casing 13 by passing the supply pipe line 25, and a temperature thereof is measured by the temperature sensor 32 at a middle of the supply pipe line 25. The heater control circuit 31 controls the heat generating amount by the heater 30 by feedback control based on a result of measurement of the temperature sensor 32.

Thereby, the cold wind A1 is supplied to the inside of the casing 13 in a state of being firmly adjusted to a desired temperature. Further, the cold wind A1, which becomes the gas A2 by being supplied to the inside of the casing 13, is exhausted to the outside of the casing 13 by passing the exhaust pipe line 26 by the fan 28, and becomes again the cold wind A1, the temperature of which is controlled to be supplied to the inside of the casing 13.

That is, the fan 28, the heat exchanger 29, the heater 30, the heater control circuit 31 and the temperature sensor 32 constitute cold wind supplying means 33 for circulating the cold wind A1 in an order of the supply pipe line 25, the casing 13 and the exhaust pipe line 26. Further, the supply pipe line 25, the exhaust pipe line 26 and the cold wind supplying means 33 constitute the temperature adjusting means 15.

Further, according to the embodiment, the temperature of the cold wind A1 is adjusted to 10° C. such that a surrounding temperature of the enveloped block B is converged to a range of 5° C. through 20° C.

Further, an upper side of the fixed base 10 is attached with a horizontal guide rail 40 extended in, for example, X direction the same as the direction of the guide rail 21 by a support portion, not illustrated. The horizontal guide rail 40 is extended to outside of the casing 13 by passing the outlet/inlet formed at one of the side faces of the casing 13. Further, outside of the casing 13 is provided with a water tank 41 storing water (liquid) W, slide glass containing shelves 42 containing unused slide glass G, and containing shelves 43 for containing the fabricated sliced piece sample H successively from a side of the casing 13 in a state of being disposed on a lower side of the horizontal guide rail 40.

Further, at the inside of the casing 13, the horizontal guide rail 40 is attached with a horizontal stage 45 movable along the horizontal guide rail 40. Further, the horizontal stage 45 is attached with an arm portion 46 movable in Z direction and capable of adsorbing at the tip thereof the sliced piece B1 cut out from the enveloped block B by utilizing, for example, static electricity. Further, the sliced piece B1 may be caught not only by static electricity but by utilizing a suction force or an adhesive. Further, the arm portion 46 carries the adsorbed sliced piece B1 to the water tank 41 provided outside of the casing 13 by passing the outlet/inlet to be dipped in stored water W. That is, the horizontal guide rail 40, the horizontal stage 45 and the arm portion 46 constitute the sliced piece handling mechanism 14.

Further, the horizontal guide rail 40 is attached with a horizontal stage 50 movable along the horizontal guide rail 40 at outside of the casing 13 in addition to the horizontal stage 45. Further, the horizontal stage 50 is made not only to simply move in the horizontal direction, but is made rotatable around Z axis. The horizontal stage 50 is attached with a slide glass grab robot 51 in a state of being rotatable around one axis orthogonal to Z direction. Further, the slide glass grab robot 51 includes a pair of arm portions 51a arranged in parallel with each other in a state of being remote from each other by a constant distance and capable of adjusting a distance therebetween to be able to proximate to each other and remote from each other.

Further, by respectively pertinently operating the horizontal stage 50 and the slide glass grab robot 51, the sliced piece sample H can be fabricated by grabbing unused slide glass G from the slide glass containing shelves 42 and transcribing the sliced piece B1 floated inside of the water tank 41 onto the grabbed slide glass G. Further, the fabricated sliced piece sample H can be contained to the containing shelves 43. A detailed explanation will be given thereof later.

The horizontal guide rail 40, the horizontal stage 50 and the slide glass grab robot 51 constitute the slide glass handling robot 5.

Further, according to the embodiment, the horizontal guide rail 40 constitutes a part that constitutes both of the sliced piece handling mechanism 14 and the slide glass handling robot 5.

Figure 3:
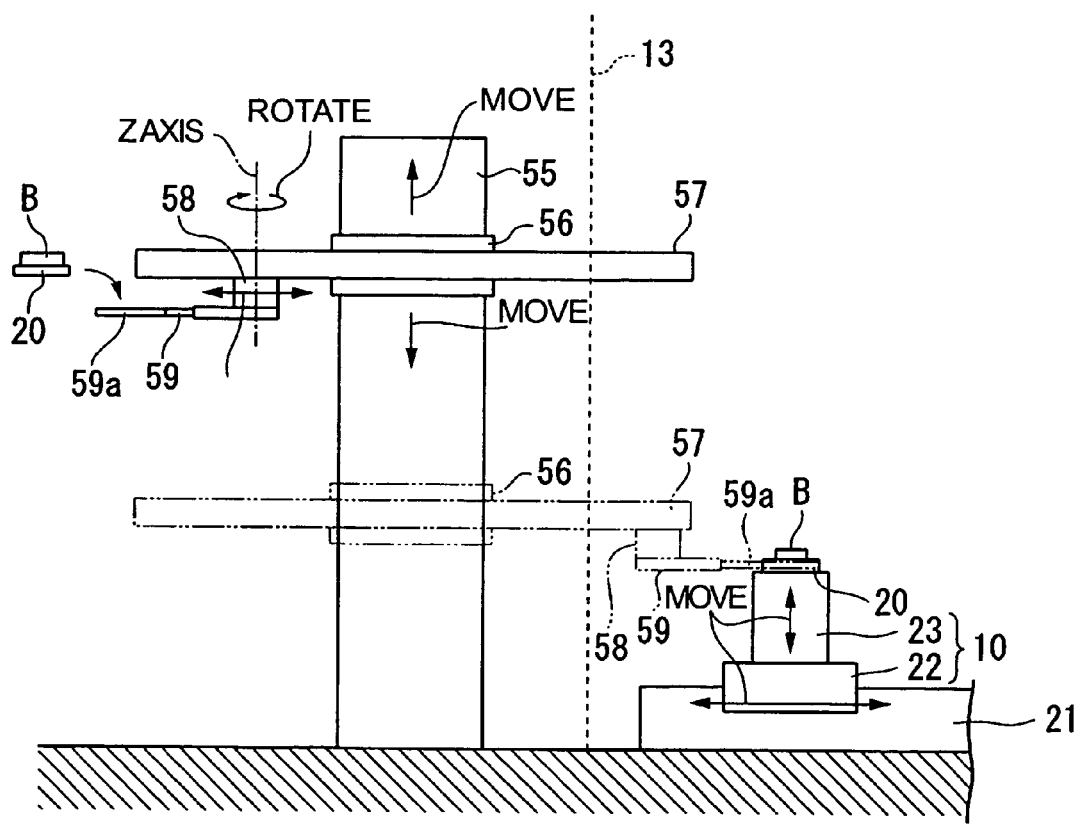
FIG. 3 is a side view showing a block handling robot of the automatic sliced piece sample fabricating apparatus shown in FIG. 1.
Figure 4:
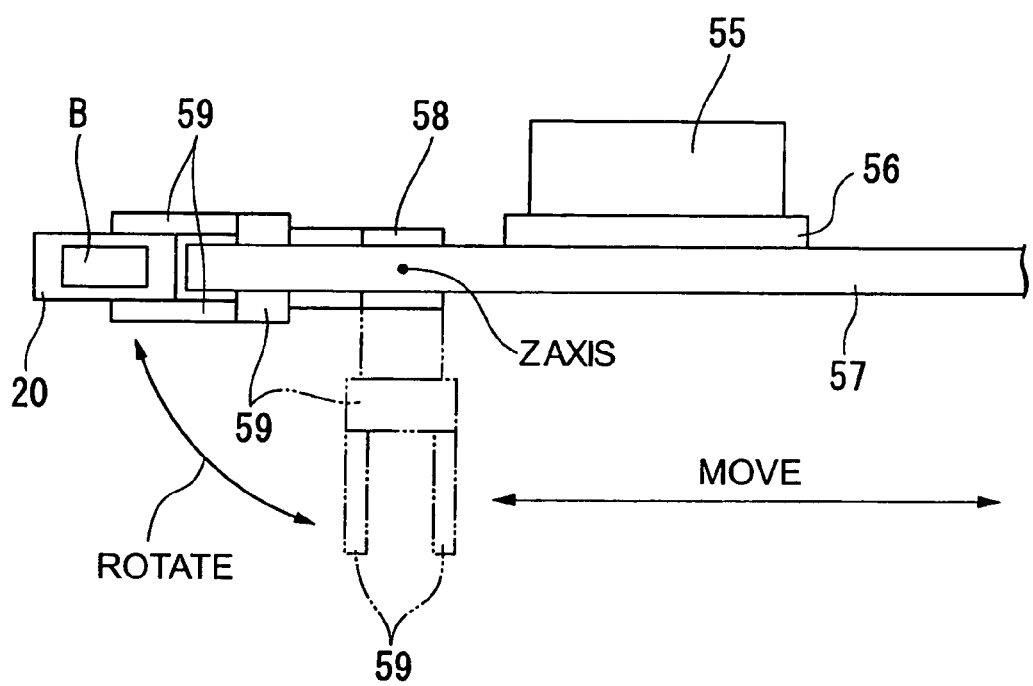
FIG. 4 is a top view of the block handling robot shown in FIG. 3.

Further, as shown by FIG. 1, FIG. 3 and FIG. 4, the outside of the casing 13 is attached with Z axis guide rail 55 extended in Z direction. The Z axis guide rail 55 is attached with a lift stage 56 movable along the Z axis guide rail 55. Further, the lift stage 56 is attached with a horizontal guide rail 57 extended in the horizontal direction. In this case, one end side of the horizontal guide rail 57 is extended to the inside of the casing 13 by passing the other outlet/inlet of the casing 13. Further, the horizontal guide rail 57 is attached with a horizontal stage 58 movable along the horizontal guide rail 57. Further, the horizontal stage 58 is made not simply to move in the horizontal direction but is made rotatable around Z axis.

Further, the horizontal stage 58 is attached with a grab robot 59 having a pair of arm portions 59a arranged in parallel with each other in a state of being remote from each other by a constant distance and capable of adjusting a distance therebetween to be able to be proximate to each other and remote from each other. Further, by respectively pertinently operating the lift stage 56, the horizontal stage 58, and the grab robot 59, the enveloped block B can be carried from outside of the casing 13 onto the fixed base 10. A detailed explanation will be given thereof later.

The Z axis guide rail 55, the lift stage 56, the horizontal guide rail 57, the horizontal stage 58 and the grab robot 59 constitute the block handling robot 2.

Next, an explanation will be given of fabricating several sheets of the sliced piece samples H from the enveloped block B by the automatic sliced piece sample fabricating apparatus 1.

First, an operator disposes the previously cooled enveloped block B to between the pair of arm portions 59a provided to the grab robot 59 of the block handling robot 2. Then, as shown by FIG. 4, the grab robot 59 receives the enveloped block B from the operator by squeezing the cassette 20 mounted with the enveloped block B by the pair of arm portions 59a. Further, after receiving the enveloped block B, the block handling robot 2 carries the enveloped block B to the inside of the casing 13 as shown in FIG. 3 by way of the outlet/inlet to be mounted on the fixed base 10 by pertinently operating the lift stage 56 and the horizontal stage 58 while pinching the cassette 20.

When the enveloped block B is mounted on the fixed base 10, the horizontal stage 45 of the sliced piece handling mechanism 14 is moved along the horizontal guide rail 40 and a front end of the arm portion 46 is brought into a standby state at a vicinity of a position of starting to cut the enveloped block B.

Next, the X stage 22 is moved along the guide rail 21 to slice the enveloped block B in a sheet-like shape by a predetermined thickness (for example, 5 μm) by the cutting blade 11. Thereby, the sliced piece B1 is cut out from the enveloped block B. On the other hand, the arm portion 46, the front end of which is at standby at a vicinity of the position of starting to cut the enveloped block B, adsorbs the sliced piece sample B1, which is started to be cut out from the enveloped block B by the cutting blade 11 by static electricity. Further, in accordance with movement of the X stage 22, the horizontal stage 45 attached with the arm portion 46 is moved along the horizontal guide rail 40. Thereby, the sliced piece B1 can firmly be adsorbed to a front end of the arm portion 46 without exerting an external force to the sliced piece B1.

After adsorbing the sliced piece B1 at the front end of the arm portion 46, the sliced piece handling mechanism 14 carries the sliced piece B1 from the one outlet/inlet to the outside of the casing 13 by moving the horizontal stage 45. Further, when the arm portion 46 reaches the upper side of the water tank 41 provided to the elongating mechanism 4, the front end is put into the water W by moving down the arm portion 46 in Z direction. Thereby, the sliced piece B1 which has been adsorbed to the front end of the arm portion 46 is dipped to be floated in water W by releasing the adsorption. The sliced piece B1 dipped into water W is brought into an elongated state by elongating wrinkle or roundness produced in cutting the surface tension.

On the other hand, in accordance with cutting out and carrying the sliced piece B1, the slide glass handling robot 5 takes out one sheet of the unused slide glass G from the slide glass containing shelves 42 to be at standby on the upper side of the water tank 41 by pertinently operating the horizontal stage 50 and the slide glass grab robot 51.

That is, first, by pertinently operating the horizontal stage 50 and the slide glass grab robot 51, the pair of arm portions 51a of the slide glass grab robot 51 are inserted to the slide glass containing shelves 42. Next, one sheet of unused slide glass G is pinched to be fixed by operating the pair of arm portions 51a to be proximate to each other. Further, the slide glass G is drawn out to be moved to the upper side of the water tank 41 by pertinently operating the horizontal stage 50 and the slide glass grab robot 51 again while pinching the slide glass G. Further, the slide glass grab robot 51 is at standby state until the sliced piece B1 is carried to the water tank 41.

After an elapse of a constant period of time of a state of dipping the sliced piece B1 into the water tank 41 as mentioned above, as shown by FIG. 1, the slide glass handling robot 5 scoops up the sliced piece B1 floated on water W by using the grabbed slide glass G by pertinently operating the horizontal stage 50 and the slide glass grab robot 51. Whereby, the sliced piece B1 is transferred onto the slide glass G. As a result, the sliced piece sample H is fabricated. Finally, the slide glass handling robot 5 carries the fabricated sliced sample H to the containing shelves 43 for storage.

As described above, according to the automatic sliced piece sample fabricating apparatus 1 of the embodiment, the sliced piece sample H can automatically be fabricated from the enveloped block B and the fabricated sliced piece sample H can be stored to the containing shelves 43. Therefore, a burden on the operator can be alleviated. Further, by reciprocally moving the X stage 22 along the X guide rail 21, the sliced piece sample H can be fabricated by automatically fabricating a necessary number of sheets of the sliced pieces B1 from the one enveloped block B.

Further, when the necessary number sheets of the sliced pieces B1 have been finished to fabricate, the block handling robot 2 carries the used enveloped block B from above the fixed base 10 to outside of the casing 13. Thereby, the operator can switch the used enveloped block B to a new successive one of the enveloped block B. Further, by repeating the above-described respective steps, a necessary number of sheets of the sliced piece sample H can automatically be fabricated from the next enveloped block B.

Particularly, since the automatic sliced piece sample fabricating apparatus 1 of the embodiment includes the automatic sliced piece fabricating apparatus 3 including the temperature adjusting means 15, before the enveloped block B is carried to inside of the casing 13 by the block handling robot 2, the cold wind A1, the temperature of which is controlled, is supplied to the inside of the casing 13 previously. That is, the cold wind A1 is supplied to the inside of the casing 13 by transporting the gas A2 cooled by the heat exchanger 29 to the supply pipe line 25 by the fan 28. At this occasion, the cold wind A1 at a desired temperature (that is, cold wind A1 at 10° C.) can firmly be supplied to the inside of the casing 13 since the temperature of the cold wind A1 is adjusted by heating the heater 30 based on the temperature of the cold wind A1 (temperature of the cold wind A1 flowing inside of the supply pipe line 25) measured by the temperature sensor 32 by the heater control circuit 31. Further, the cold wind temperature is a temperature calculated such that the temperature surrounding the enveloped block B is converged into the range of 5° C. through 20° C.

Therefore, according to the previously cooled enveloped block B, the surrounding is cooled by the cold wind A1 after having been mounted on the fixed base 10 and therefore, the surface temperature is difficult to rise with an elapse of time different from that in the related art. Particularly, although according to the related art, the lower face of the enveloped block B is simply cooled, according to the embodiment, the temperature of the surrounding of the enveloped block B is directly adjusted by supplying the cold wind A1. Therefore, the surface temperature of the enveloping agent, whose major component is constituted by paraffin having the small heat conduction coefficient, can easily be adjusted accurately. In addition thereto, also by utilizing air having a small heat capacity per volume as the cold wind A1, the temperature is easy to be adjusted. Further, since the cold wind A1 is utilized, an influence is not effected on cutting out the sliced piece B1 by the cutting means at all.

In this way, since the temperature adjusting means 15 is provided, during a time period until finishing to fabricate the sliced piece B1 after carrying the sliced piece B1 onto the fixed base 10 by the block handling robot 2, a temperature change of the surface of the enveloped block B can be restrained. Therefore, a mechanical property of hardness, friction coefficient, or viscosity of paraffin is difficult to be changed. As a result, the enveloped block B can be cut by the same condition and the uniform and high quality sliced piece B1 can be fabricated.

Therefore, also the sliced piece sample H fabricated by using the sliced piece B1 can similarly be provided with high quality. Therefore, accuracy of various tests or inspections using the sliced piece sample H can be promoted and reliability can be promoted.

Further, the cold wind A1 supplied to the inside of the casing 13 becomes the gas A2 to fill the inside of the casing 13 after cooling at least a surrounding of the enveloped block B. Here, since the exhaust pipe line 26 is provided at the inside of the casing 13, the gas A2 is sucked to the fan 28 by passing the exhaust pipe line 26. Further, the sucked gas A2 is blown to the heat exchanger 29 by the fan 28 to become the cold wind A1 again to be supplied to the inside of the casing 13. In this way, the cold wind A1 is made to flow by the cold wind supplying means 33 while being circulated without interruption in an order of the supply pipe line 25, the casing 13 and the exhaust pipe line 26.

Therefore, the surrounding of the enveloped block B carried to the inside of the casing 13 can efficiently be cooled, and the temperature of the surface of the enveloped block B can further be cooled. Further, since the cold wind A1 is circulated, the cold wind A1 can efficiently be supplied and low cost formation can be achieved.

Next, an explanation will be given of a second embodiment of the automatic sliced piece sample fabricating apparatus according to the invention in reference to FIG. 5. Further, portions of the second embodiment the same as constituent elements in the first embodiment are attached with the same notations and an explanation thereof will be omitted.

Although according to the first embodiment, the surface of the enveloped block B is cooled by supplying the cold wind A1 to the inside of the casing 13, according to the second embodiment, the surface temperature of the enveloped block B is further accurately controlled by locally blowing the cold wind A1 to the surface of the enveloped block B by an automatic sliced piece fabricating apparatus 60.

Figure 5:
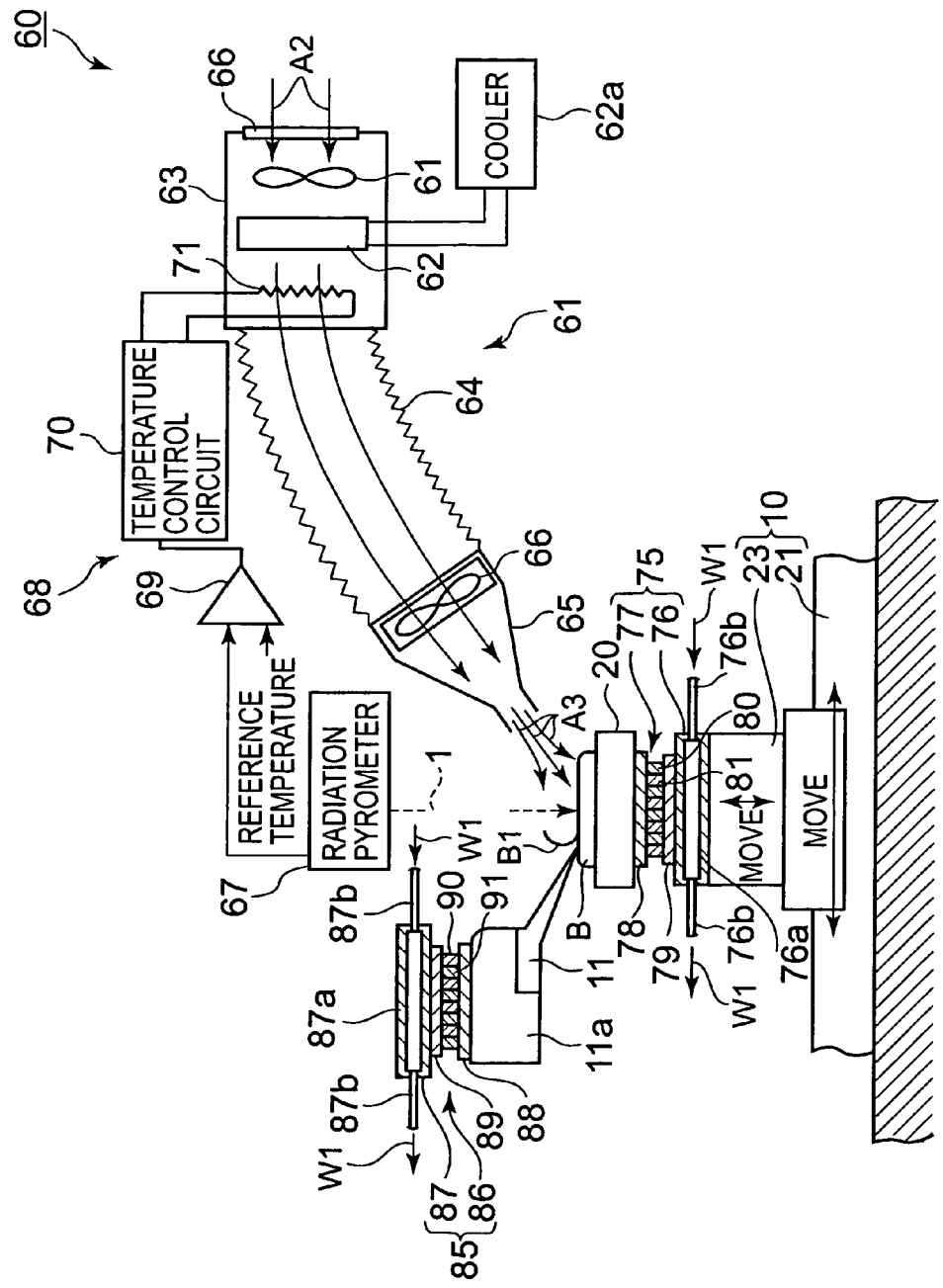
FIG. 5 is a constitution view showing a second embodiment of an automatic sliced piece fabricating apparatus according to the invention.

That is, as shown by FIG. 5, the automatic sliced piece fabricating apparatus 60 of the embodiment includes cold wind blowing means 61 arranged inside of the casing 13 for locally blowing cold wind A3 (second cold wind), a temperature of which is controlled to the surface of the enveloped block B.

Specifically, the cold wind blowing means 61 includes a fan 62, a box 63 including a heat exchanger 62 connected to a cooler 62a, a flexible pipe 64 having a flexibility, one end side of which is connected to the box 63, and a cold wind blow out port 65 connected to other end side of the flexible pipe 64.

The fan 62 takes in the gas A2 at the inside of the casing 13 through a filter 66 attached to a side face of the box 63 to blow to the heat exchanger 62. The heat exchanger 62 is circulated with a cold medium transported from the cooler 62a at the inside thereof and adsorbs heat of the gas A2 blown by the fan 62. Thereby, the gas A2 is cooled to become the cold wind A3 to be supplied to the inside of the flexible pipe 64.

The flexible pipe 64 is a pipe in a bellows-like shape, and is adjusted such that a front end of the cold wind blow out port 65 connected to other end side is disposed at a vicinity of the surface of the enveloped block B. According to the embodiment, the flexible pipe 64 is moved in synchronism with movement of the X stage 22, and the front end of the cold wind blow out port 65 is disposed always at a vicinity of the surface of the enveloped block B.

The cold wind blow out port 65 is constituted by a shape tapered to the front end to be able to locally blow the cold wind A3 further concentratedly. Further, the inside of the cold wind blow out port 65 includes a fan 66 to thereby assist the cold wind A3 to blow out firmly by increasing a speed of the cold wind A3 passing through the flexible pipe 64.

Further, the cold wind blowing means 61 according to the embodiment includes a radiation pyrometer (temperature measuring means) 67 for measuring the surface temperature of the enveloped block B in noncontact, and a temperature adjusting mechanism (second temperature adjusting means) 68 for adjusting a temperature of the cold wind A3 such that the surface temperature of the enveloped block B becomes 10° C. based on a temperature measured by the radiation pyrometer.

The radiation pyrometer 67 measures the temperature in a noncontact state by radiating infrared ray I to the surface of the enveloped block B moved along with the X stage 22 and outputs the measured temperature to a comparing portion 69. The comparing portion 69 compares the transmitted measured temperature with a previously set reference temperature (for example, 10° C. in a range of 5° C. through 20° C.) and outputs a temperature difference thereof to a temperature control circuit 70. The temperature control circuit 70 controls the temperature of the cold wind A3 by heating the heater 71 provided inside of the box 63 to be disposed between the heat exchanger 62 and the flexible pipe 64 to nullify the transmitted temperature difference (to be proximate "0"). Thereby, the surface temperature of the enveloped block B (for example, a temperature in a range of from the surface to a depth of 5 μm) is maintained at 10° C. by the cold wind A3.

The comparing portion 69, and the temperature control circuit 70 and the heater 71 constitute the temperature adjusting mechanism 68.

Further, the automatic sliced piece fabricating apparatus 60 of the embodiment is integrated with a fixed base cooling mechanism 75 for cooling the enveloped block B to an arbitrary temperature by being brought into contact with the enveloped block B at the fixed base 10. That is, a cooling block 76 and a Pertier element 77 are successively attached onto the Z stage 23, and the cassette 20 for fixing the enveloped block B is mounted on the Pertier element 77.

The Pertier element 77 includes a pair of base plates 78, 79 having an electrically insulating property of alumina or aluminum nitride and a p-type thermoelectric material 80 and an n-type thermoelectric material 81 arranged between the pair of base plates 78, 79. The p-type thermoelectric material 80 and the n-type thermoelectric material 81 are subjected to PN junction by an electrode, not illustrated, and are electrically connected in series.

A surface of the base plate 78 on one side of the pair of base plate 78, 79 constitutes a cooling face, and a surface of the base plate 79 on other side constitutes a heat radiating face. The direction of electrons flowing in the p-type thermoelectric material 80 and the n-type thermoelectric material 81 of the Pertier element 77 is controlled such that the base plate 78 on one side is cooled. Further, the heat radiating face of the Pertier element 77 is adhered to an upper face of the cooling block 76 by a thermally conductive grease of silicone jelly or the like, silver paste, or an adhesive. Further, by operating the Pertier element 77, the enveloped block B can firmly be cooled by way of the cassette 20 brought into face contact with the cooling face. Further, heat deprived from the enveloped block B is conducted to the cooling block 76 by way of the heat radiating face.

The cooling block 76 constitutes a cavity 76a at the inside thereof and both ends of the cavity 76a are respectively connected with tubes 76b. Further, heat conducted from the heat radiating face of the Pertier element 77 escapes as much as possible from inside of the casing 13 to the outside by making cooling water W1 flow at inside of the cavity 76a by passing through the tubes 76b.

The Pertier element 77 and the cooling block 76 constitute the fixed base cooling mechanism 75.

Further, the automatic sliced piece fabricating apparatus 60 according to the embodiment includes a cutting blade cooling mechanism 85 for cooling the cutting blade 11 by being brought into contact with the cutting blade 11 similar to the fixed base cooling mechanism 75.

A holder 11a for fixing the cutting blade 11 is fixed with a Pertier element 86 and a cooling block 87. The Pertier element 86 is constituted similar to the Pertier element 77, and includes a pair of base plates 88, 89, and a p-type thermoelectric material 90 and an n-type thermoelectric material 91. Further, a surface of the base plate 88 on one side constitutes a cooling face and a surface of the base plate 89 on other side constitutes a heat radiating face. According to the Pertier element 86, the cooling face and the heat radiating face are respectively adhered to an upper face of the holder 11a and a lower face of the cooling block 87 by various adhesives.

Therefore, the cutting blade 11 can be cooled by way of the holder 11a brought into face contact with the cooling face by operating the Pertier element 86. Further, heat deprived of the cutting blade 11 is conducted to the cooling block 87 by way of the heat radiating face.

The cooling block 87 is constituted similar to the cooling block 76 and is made to be able to escape heat conducted from the heat radiating face of the Pertier element 86 from inside of the casing 13 to the outside as much as possible by making the cooling water W1 flow to inside of a cavity 87a by passing through tubes 87b.

The Pertier element 86 and the cooling block 87 constitute the cutting blade cooling mechanism 85.

An explanation will be given of a case of fabricating the sliced piece B1 from the enveloped block B by the automatic sliced piece fabricating apparatus 60 constituted in this way.

When the enveloped block B is mounted on the fixed base 10, that is, on the cooling face of the Pertier element 77, the cold wind blowing means 61 blows the cold wind A3, the temperature of which is controlled to the surface of the enveloped block B. That is, the fan 62 takes the gas A2 at the inside of the casing 13 into the box 63 by passing through the filter 66 to be blown to the heat exchanger 62. The blown gas A2 becomes the cold wind A3 by being subjected to heat exchange by the heat exchanger 62 to be supplied to the flexible pipe 64. Further, the cold wind A3 passing through the flexible pipe 64 is firmly blown from the front end of the cold wind blow out port 65 to the surface of the enveloped block B by increasing the speed by the fan 66.

At this occasion, the radiation pyrometer 67 measures the surface temperature of the enveloped block B to which the cold wind A3 is blown to be transmitted to the comparing portion 69. Further, the comparing portion 69 compares the transmitted measured temperature with the previously set reference temperature (10° C.) to output the temperature difference to the temperature control circuit 70. Further, the temperature control circuit 70 controls the temperature of the cold wind A3 by heating the heater 71 to nullify the temperature difference.

Therefore, the surface temperature of the enveloped block B can be cooled and maintained at 10° C. Particularly, when paraffin included in the enveloped block B becomes a temperature equal to or higher than 20° C., the enveloped block B starts to be softened and a mechanical property is liable to be changed abruptly. However, by maintaining the surface temperature of the enveloped block B at 10° C. as in the embodiment, the mechanical property of paraffin for fabricating by the sliced piece B1 can be maintained constant. Therefore, the enveloped block B can be cut firmly under the same condition. As a result, the further uniform and high quality sliced piece B1 can be fabricated.

Further, the radiation pyrometer 67 measures the surface temperature of the enveloped block B in the noncontact state and therefore, does not effect an influence on cutting out the sliced piece B1 by the cut mechanism 12 at all.

Further, the enveloped block B can be cooled by way of the cassette 20 by operating the Pertier element 77 integrated to the fixed base 10 simultaneously with blowing the cold wind A3. Thereby, a cooling effect of the cold wind A3 blown by the cold wind blowing means 61 can be promoted, and the cooling efficiency can further be promoted. Further, heat conducted from the heat radiating face of the Pertier element 77 to the cooling block 76 can be escaped as much as possible to the outside of the casing 13 by the cooling water W1. Therefore, an influence of the heat effected on the enveloped block B can be restrained as less as possible.

Further, since the Pertier element 86 is provided also on the side of the cutting blade 11, the cutting blade 11 per se can be cooled. Thereby, in cutting out the sliced piece B1 from the enveloped block B, the sliced piece B1 can be prevented from being softened by the temperature of the cutting blade 11. Therefore, the sliced piece B1 can be prevented from sticking to the cutting blade 11, and deformation of the sliced piece B1 owing to the sticking can be prevented. Further, since the sliced piece B1 is difficult to stick to the cutting blade 11, the sliced piece B1 can easily be adsorbed by the cut piece handling mechanism 14 and the sliced piece B1 is facilitated to be carried.

Further, the technical range of the invention is not limited to the embodiments, but can variously be changed within the range not deviated from the gist of the invention.

For example, in the second embodiment, although there is constructed a constitution of simultaneously cooling the enveloped block and the cutting blade by utilizing the Pertier elements simultaneously with blowing the cold wind, only the cold wind may be blown by the cold wind blowing means. However, it is preferable to constitute a combination of all thereof simultaneously as in the second embodiment.

Further, the constitution of the first embodiment may be combined with either of the fixed base cooling mechanism or the cutting blade cooling mechanism, or may be combined with both thereof without carrying out the blowing.

Further, although according to the above-described respective embodiments, there is constructed a constitution of only providing the water tank for storing water as an elongating mechanism, the invention is not limited to the case. For example, there may be constituted an elongating mechanism provided with a water tank storing hot water and a hot plate contiguously to the above-described water tank.

In this case, after mounting the sliced piece finished with elongation by water on the slide glass, the sliced piece is carried to other water tank storing hot water to be dipped in hot water by the slide glass handling robot. The sliced piece is easy to be elongated by hot water and therefore, remaining wrinkle or roundness which cannot be removed by the elongation by water can be removed. Therefore, a further high quality sliced piece sample can be fabricated.

Further, by mounting the slide glass mounted with the sliced piece on the hot plate after the elongation by hot water, heat can further be applied to the sliced piece by way of the slide glass. Thereby, wrinkle or roundness which cannot be removed by the elongation by hot water can further be removed. In this way, by providing the water tank stored with hot water and the hot plate, a further high quality sliced piece sample can be fabricated and therefore, the constitution is further preferable.

What is claimed is:

1. An automatic sliced piece fabricating apparatus comprising:
 a fixed base for mounting an enveloped block;
 cutting means including a cutting blade arranged on the fixed base for cutting out a sliced piece from the enveloped block by moving the cutting blade and the fixed base relative to each other;
 a cabinet for containing the fixed base and the cutting means;

a sliced piece carrying means for carrying the cut-out sliced piece outside of the cabinet;

a temperature adjusting means for adjusting a temperature surrounding the enveloped block to a predetermined temperature by supplying a cold wind to the cabinet;

a cold wind blowing means arranged within the cabinet for locally blowing a second cold wind;

a temperature measuring means for measuring a surface temperature of the enveloped block in noncontact; and a second temperature adjusting means for adjusting the temperature of the second cold wind such that the surface temperature of the enveloped block becomes a desired temperature based on the temperature measured by the temperature measuring means.

2. The automatic sliced piece fabricating apparatus according to claim 1, wherein the temperature adjusting means carries out a temperature adjustment such that a surrounding temperature of the enveloped block is converged in a range of 5° C. through 20° C.

3. The automatic sliced piece fabricating apparatus according to claim 1, wherein the temperature adjusting means comprises:

a supply pipe line for supplying the cold wind to the cabinet;

an exhaust pipe line for exhausting a gas from the cabinet; and a cold wind supplying means for recirculating the gas exhausted from the exhaust pipe line into the cabinet as the cold wind.

4. The automatic sliced piece fabricating apparatus according to claim 1, wherein the fixed base is integrated with a fixed base cooling mechanism for cooling the enveloped block by contact.

5. The automatic sliced piece fabricating apparatus according to claim 1, wherein the cutting means comprises a cutting blade cooling mechanism for cooling the cutting blade by contact.

6. An automatic sliced piece sample fabricating apparatus comprising:

the automatic sliced piece fabricating apparatus according to claim 1;

a block carrying means for carrying the enveloped block from outside of the cabinet onto the fixed base;

an elongating means for elongating the sliced piece carried by the sliced piece carrying means at least by dipping the sliced piece into a liquid; and a transcribing means for transcribing the elongated sliced piece onto a base plate to fabricate a sliced piece sample.

7. An automatic sliced piece fabricating apparatus comprising:

a fixed base for mounting an enveloped block;

cutting device comprising a cutting blade, wherein the cutting device moves the cutting blade and the fixed based relative to each other to cut out a sliced piece from the enveloped block, the cutting device being arranged on the fixed base;

a cabinet containing the fixed base and the cutting device;

a sliced piece carrying device arranged to carry the cut-out sliced piece outside of the cabinet;

a temperature adjusting device that supplies a cold wind to the cabinet to adjust a temperature surrounding the enveloped block to a predetermined temperature;

a cold wind blowing device that locally blows a second cold wind, the cold wind blowing device being arranged within the cabinet;

a temperature measuring device that measures a surface temperature of the enveloped block in noncontact; and a second temperature adjusting device that adjusts the temperature of the second cold wind such that the surface temperature of the enveloped block becomes a desired temperature based on the temperature measured by the temperature measuring means.

8. The automatic sliced piece fabricating apparatus according to claim 7, wherein the temperature adjusting device carries out a temperature adjustment such that a surrounding temperature of the enveloped block is converged in a range of 5° C. through 20° C.

9. The automatic sliced piece fabricating apparatus according to claim 7, wherein the temperature adjusting device comprises:

a supply pipe line for supplying the cold wind to the cabinet;

an exhaust pipe line for exhausting a gas from the cabinet; and a cold wind supplying device that recirculates the gas exhausted from the exhaust pipe line into the cabinet as the cold wind.

10. The automatic sliced piece fabricating apparatus according to claim 7, wherein the fixed base is integrated with a fixed base cooling mechanism for cooling the enveloped block by contact.

11. The automatic sliced piece fabricating apparatus according to claim 7, wherein the cutting device comprises a cutting blade cooling mechanism for cooling the cutting blade by contact.

* * * * *

UNITED STATES PATENT AND TRADEMARK OFFICE
CERTIFICATE OF CORRECTION

PATENT NO. : 7,802,507 B2
APPLICATION NO. : 11/651714
DATED : September 28, 2010
INVENTOR(S) : Tetsumasa Ito et al.

Page 1 of 1

It is certified that error appears in the above-identified patent and that said Letters Patent is hereby corrected as shown below:

In column 17, claim 2, line 19, before "through" replace "5° C." with --5°C--.

In column 18, claim 7, line 6, before "relative to each other" replace "based" with --base--.

In column 18, claim 8, line 29, before "through" replace "5° C." with --5°C--.

Signed and Sealed this
Twelfth Day of April, 2011

David J. Kappos
*Director of the United States Patent and Trademark Office*